(12) United States Patent
Wawro

(10) Patent No.: US 11,331,014 B2
(45) Date of Patent: May 17, 2022

(54) COMPACT, ENERGY EFFICIENT PHYSIOLOGICAL PARAMETER SENSOR SYSTEM

(71) Applicant: Welch Allyn, Inc., Skaneateles Falls, NY (US)

(72) Inventor: Thaddeus J. Wawro, Auburn, NY (US)

(73) Assignee: Welch Allyn, Inc., Skaneateles Falls, NY (US)

(*) Notice: Subject to any disclaimer, the term of this patent is extended or adjusted under 35 U.S.C. 154(b) by 512 days.

(21) Appl. No.: 15/962,380

(22) Filed: Apr. 25, 2018

(65) Prior Publication Data

US 2019/0282144 A1    Sep. 19, 2019

Related U.S. Application Data

(60) Provisional application No. 62/642,819, filed on Mar. 14, 2018.

(51) Int. Cl.
    *A61B 5/1455*    (2006.01)
    *A61B 5/00*      (2006.01)

(52) U.S. Cl.
    CPC ........ *A61B 5/14552* (2013.01); *A61B 5/7275* (2013.01); *A61B 2562/046* (2013.01); *A61B 2562/164* (2013.01); *A61B 2562/185* (2013.01)

(58) Field of Classification Search
    None
    See application file for complete search history.

(56) References Cited

U.S. PATENT DOCUMENTS

| 8,798,702 B2 * | 8/2014 | Trumble ............ A61B 5/14551 |
| | | 600/323 |
| 8,823,944 B2 | 9/2014 | Yamashita et al. |
| | (Continued) | |

FOREIGN PATENT DOCUMENTS

| EP | 3033992 A1 | 6/2016 |
| EP | 3238615 A1 | 11/2017 |
| WO | 2015171667 A1 | 12/2015 |

OTHER PUBLICATIONS

WPI; Reflectance-Based Pulse Oximeter For The Chest and Wrist; A Major Qualifying Report: Submitted to the Faculty Of the Worcester Polytechnic Institute In partial fulfillment of the requirements for the Degree of Bachelor of Science By Alexandra Frontaine, Arben Koshi, Danielle Morabito, Nicolas Rodriguez.. Approved by Professor Yitzhak Mendelson, Advisor, Dept. of Biomedical Engineering; part 1 pp. 1-43.

(Continued)

*Primary Examiner* — Marjan Fardanesh
(74) *Attorney, Agent, or Firm* — Merchant & Gould P.C.

(57) ABSTRACT

A physiological parameter sensor system includes a housing with a first cell and a plurality of second cells. A first sensor system element (either an emitter or a detector) resides in the first cell. Second sensor system elements reside in at least some of the second cells. If the first sensor system element is an emitter, each second sensor system element is a detector, and vice versa. The housing is conformable to the contours of a patient to ensure that the sensor system elements are closely coupled to the patient's skin. The system identifies the emitter which yields the best quality signal at the detector (or the detector which receives the best quality signal from the emitter). The system then uses only (Continued)

the identified emitter/detector pair. The system is compact, places only modest demands on battery power, and tolerates being positioned at a nonoptimal locations on the patient's body.

13 Claims, 9 Drawing Sheets

(56) References Cited

U.S. PATENT DOCUMENTS

| | | | |
|---|---|---|---|
| 8,958,860 | B2 | 2/2015 | Banerjee et al. |
| 8,986,207 | B2 | 3/2015 | Li et al. |
| 9,901,261 | B2 | 2/2018 | McCombie et al. |
| 2014/0213862 | A1 | 7/2014 | Addison et al. |
| 2015/0057511 | A1 | 2/2015 | Basu |
| 2015/0141774 | A1 | 5/2015 | Ogawa et al. |
| 2015/0230743 | A1 | 8/2015 | Silveira et al. |
| 2015/0238098 | A1 | 8/2015 | Park et al. |
| 2015/0374245 | A1 | 12/2015 | Szilagyi |
| 2016/0081603 | A1 | 3/2016 | Peng et al. |
| 2016/0120411 | A1 | 5/2016 | Hadley et al. |
| 2016/0287108 | A1 | 10/2016 | Wei et al. |
| 2017/0135617 | A1 | 5/2017 | Alasirnio et al. |
| 2017/0265753 | A1 | 9/2017 | Boettcher et al. |
| 2017/0325698 | A1 | 11/2017 | Allec et al. |
| 2018/0055389 | A1 | 3/2018 | Banet et al. |

OTHER PUBLICATIONS

WPI; Reflectance-Based Pulse Oximeter For The Chest and Wrist; A Major Qualifying Report: Submitted to the Faculty Of the Worcester Polytechnic Institute In partial fulfillment of the requirements for the Degree of Bachelor of Science By Alexandra Frontaine, Arben Koshi, Danielle Morabito, Nicolas Rodriguez.. Approved by Professor Yitzhak Mendelson, Advisor, Dept. of Biomedical Engineering; part 2 pp. 44-86.

WPI; Reflectance-Based Pulse Oximeter For The Chest and Wrist; A Major Qualifying Report: Submitted to the Faculty Of the Worcester Polytechnic Institute In partial fulfillment of the requirements for the Degree of Bachelor of Science By Alexandra Frontaine, Arben Koshi, Danielle Morabito, Nicolas Rodriguez.. Approved by Professor Yitzhak Mendelson, Advisor, Dept. of Biomedical Engineering; part 3 pp. 87-130.

Extended European Search Report dated Jul. 30, 2019; Applicant Welch Allyn, Inc.; Application No. 19162313.1-1132; Place of Search—Berlin; Date of completion—Jul. 22, 2019.

Correspondence from Reddie & Grose dated Mar. 3, 2020; European Patent Application No. 19162313.1; Compact, Energy Efficient Physiological Parameter Sensor System of Welch Allyn, Inc.; Reference P/80061.EP01/AF/IXW; 5-pages.

Claims (clean version) of European Application No. 19162313.1 pp. 19, 20, 21, 22, 23, and 24.

Claims (marked version) of European Application No. 19162313.1 pp. 19, 20, 21, 22, 23, and 24.

* cited by examiner

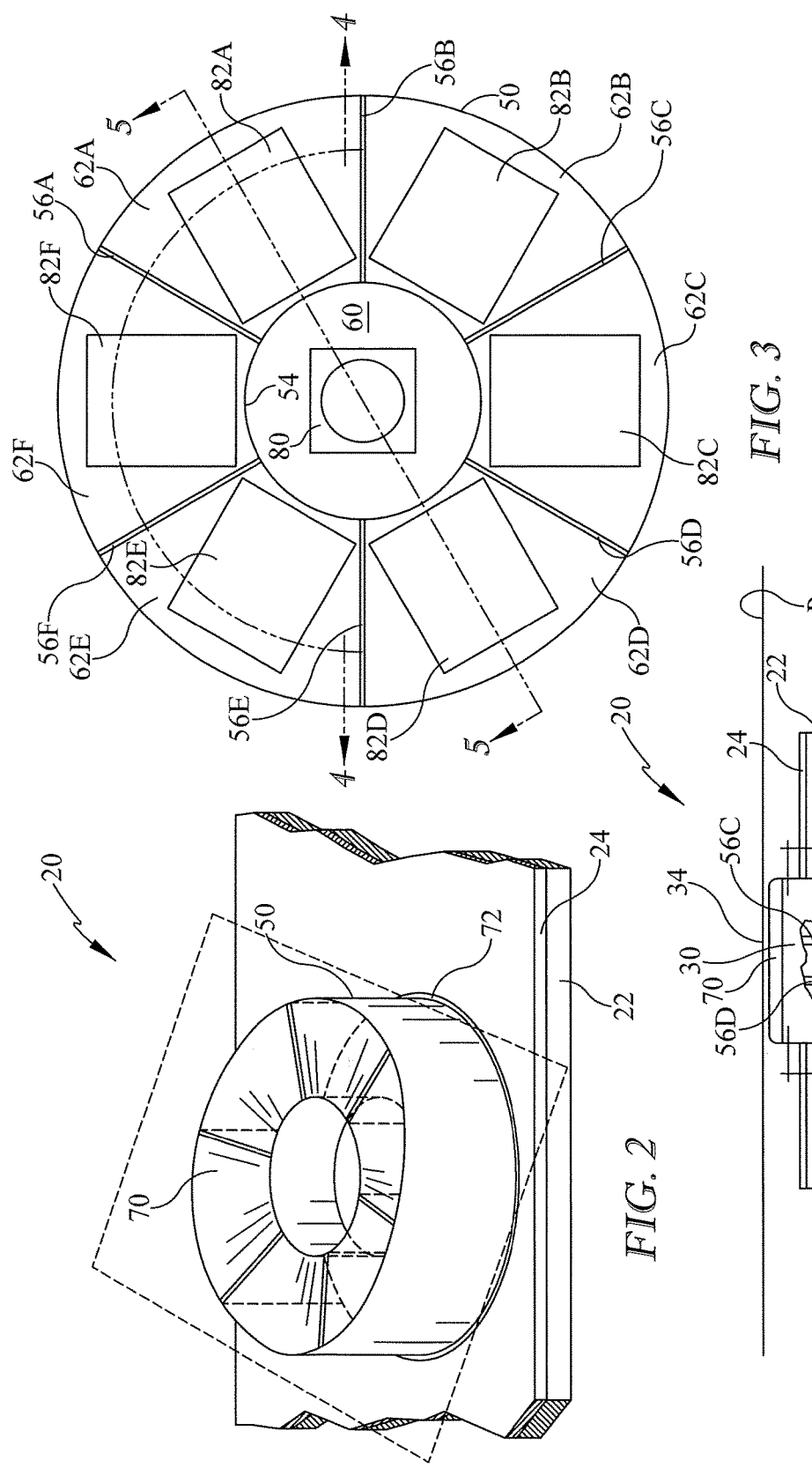

COMPACT, ENERGY EFFICIENT PHYSIOLOGICAL PARAMETER SENSOR SYSTEM

TECHNICAL FIELD

The subject matter described herein relates to physiological parameter sensor systems, in particular to a sensor system suitable for use in applications where compactness is desirable and electrical power is at a premium.

BACKGROUND

Some physiological parameter sensor systems include an emitter that emits electromagnetic energy into the tissue of a subject (e.g. a hospital patient) and a detector that detects a return signal associated with the emitted signal. A processor uses information about one or more properties of the emitted and return signals to estimate a physiological parameter.

One example of such a system is a reflectance pulse oximeter which determines the oxygen saturation ($SpO_2$) of the hemoglobin of a subject, such as a medical patient. The oximeter has one or more emitters for emitting red light and infrared light. The oximeter also includes a photodetector. A processor causes the emitters to illuminate a tissue site alternately with red and infrared light. (As used throughout this specification, "light" is not limited to the visible portion of the electromagnetic spectrum.) Light which returns to the pulse oximeter as a result of the illuminations with red and infrared light is detected by the photodetector. A processor estimates the patient's blood oxygen saturation in a well known manner as a function of the intensity of light received at the photodetector in response to the red illumination and the infrared illumination during both pulsatile and nonpulsatile phases of the patient's heart cycle.

Oximeters as just described, and other monitors which employ emitted and reflected energy to determine physiological parameters, may be designed to be worn by a patient or may be designed to be one sensing component of a wearable device that also includes other types of sensors. Such monitors may include an adhesive layer for attaching the monitor to the patient's skin. Wearable sensors are advantageous because they can provide continuous monitoring of the patient. Wearable monitors that rely on onboard battery power, rather than being attached to an electrical power source by a wire, are advantageous also because they offer the patient greater freedom of movement. One drawback of battery powered wearable monitors is that their useful life depends in part on how much demand their electrical components, such as emitters and detectors, place on the battery. It is therefore helpful to keep power demands as small as possible, for example small enough that the battery will last at least five days.

Another consideration in the design of wearable monitors is related to their physical size. Larger monitors will be more objectionable to the patient than a smaller monitor. Larger monitors will also be less likely to adhere reliably to the patient for an extended time. Compactness is therefore desirable.

Yet another consideration in the design of wearable monitors is related to placement of the monitor on the patient's body. The general location for attachment of the monitor is known. However the exact location required for best operation varies from patient to patient. If the monitor includes an adhesive layer for attaching it to the patient's skin, the suitability of a selected location is not known until after a caregiver has adhered the monitor to the patient's skin. If the monitor operates poorly it may be necessary to remove it from its original position and reapply it at a different location. Removal of the monitor may cause patient discomfort. Moreover the adhesive properties of the adhesive may be compromised enough that the monitor cannot be reliable secured to another site on the patient's body. In that case the caregiver must discard the wearable monitor and use a new one.

One way to avoid the foregoing problem with monitor placement is to allow the emitter, detector and other electrically powered components to draw enough battery power that even a poorly positioned monitor will operate satisfactorily. However doing so either reduces battery life or requires a physically larger battery, and therefore a physically larger monitor. Reduced battery life and increased monitor size are both contrary to the objectives of long life and compactness described above. It is, therefore, desirable to instead provide a monitor which operates satisfactorily even if suboptimally positioned on the patient's body.

Another consideration in the design of a wearable monitor is ensuring that the emitter and detector are closely coupled to the patient's skin.

Accordingly, what is needed is a physiological monitor that is compact enough to be wearable, places only modest demands on battery power, is tolerant to being positioned at a nonoptimal location on the patient's body, and whose sensor system elements are closely coupled to the patient's skin.

SUMMARY

The present invention may comprise one or more of the features recited in the appended claims and/or one or more of the following features or combinations thereof.

A physiological parameter sensor system includes a housing having a patient facing side having a baseline configuration, an opposite side longitudinally spaced from the patient facing side, and a set of longitudinally extending sidewalls which cooperate with the patient facing side and the opposite side to define a first cell and a plurality of second cells. The plurality of second cells circumscribes the first cell. A first sensor system element resides in the first cell. The first sensor system element is either an emitter or a detector. Two or more second sensor system elements reside in at least some of the plurality of second cells. If the first sensor system element is an emitter, each second sensor system element is a detector, and vice versa. The patient facing side of the housing is conformable to a non-baseline configuration.

BRIEF DESCRIPTION OF THE DRAWINGS

The foregoing and other features of the various embodiments of the physiological parameter sensor system described herein will become more apparent from the following detailed description and the accompanying drawings in which:

FIG. 1 is a cross sectional side elevation view of a schematically illustrated wearable device which includes a physiological parameter sensor system having a housing which is shown in a baseline state. The housing includes a perimeter wall (broken away to reveal internal sidewalls), a patient side closure element, and an opposite side closure element.

FIG. 2 is a perspective view of a device of the type shown in FIG. 1. showing the housing in a nonbaseline state.

FIG. 3 is a plan view taken along 3-3 of FIG. 1.

DETAILED DESCRIPTION

Figure 4:
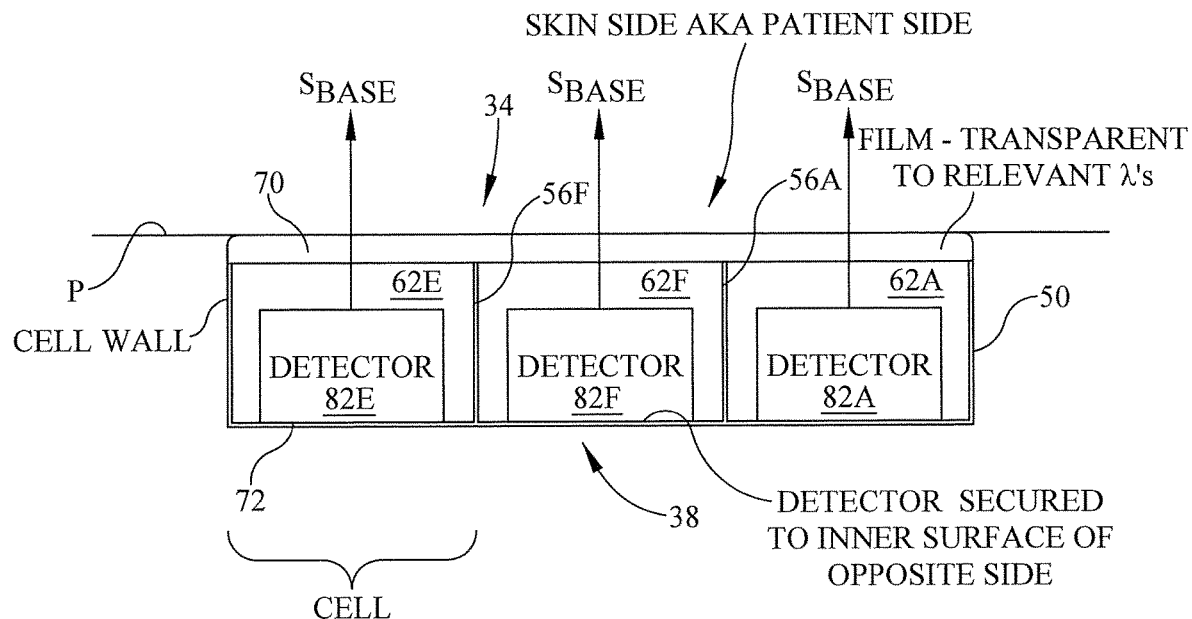
FIG. 4 is an unwrapped sectional view along 4-4 of FIG. 3 showing an embodiment in which internal walls are common to neighboring cells, and showing the housing in a baseline state or configuration.

In this specification and drawings, features similar to or the same as features already described may be identified by reference characters or numerals which are the same as or similar to those previously used. Similar elements may be identified by a common reference character or numeral, with suffixes being used to refer to specific occurrences of the element.

Referring to FIGS. 1-6, a wearable device 20 comprises a base 22 with a layer 24 of adhesive and a cap 26. The device includes a physiological parameter sensor system having a housing 30 which projects slightly beyond base 22 and adhesive 24. When the device is in use the adhesive layer secures the device to a patient's skin S as seen best in FIG. 6. Accordingly, side 34 of the housing is considered to be the patient side of the housing and side 38 is considered to be the opposite side of the housing. Opposite side 38 is longitudinally spaced from patient side 34.

Housing 30 comprises a housing sidewall 50, also referred to as a perimeter wall. Other longitudinally extending sidewalls extend from the patient side of the housing to the opposite side of the housing. In the illustrated embodiment the other sidewalls include a hub sidewall 54, and radial sidewalls 56 extending radially between the hub sidewall and the housing sidewall. The hub sidewall and radial sidewalls cooperate with housing perimeter wall 50, patient side 34, and opposite side 38 of the housing to define a first cell 60 and a plurality of second cells 62. Taken collectively, the second cells circumscribe the first cell so that the first cell is a central cell and the plurality of second cells radially neighbor the central cell. The cells extend longitudinally from the patient side of the housing to the opposite side of the housing. Hub sidewall 54 and radial sidewalls 56 are intercell walls which are common to adjacent cells.

In the illustrated embodiment the patient side 34 of the housing is a patient side closure element such as a membrane 70, and the opposite side 38 of the housing is an opposite side closure element such as a cover 72. The patient side closure element guards against contaminant ingress into the interior of the housing. Contaminants of concern include fluids, dust, acoustic energy and electromagnetic energy. Each sidewall extends longitudinally from the patient side closure element to the opposite side closure element where the sidewall abuts or is joined to the closure element.

Figure 7:
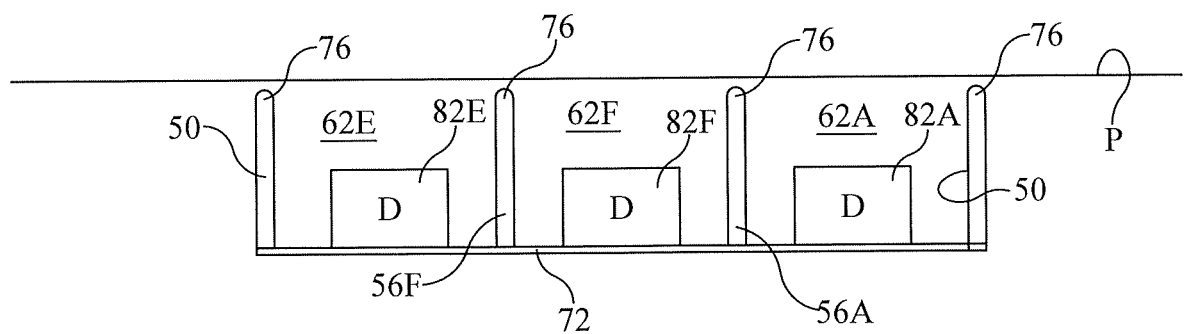
FIG. 7 is a view similar to that of FIG. 4 showing an embodiment which does not include a patient side closure element.

In other embodiments one or both closure elements may be absent. In such embodiments the longitudinal extremities of the sidewalls are referred to as free extremities or free termini 76. FIG. 7 shows an example embodiment in which the opposite side closure element 72 is present but there is no patient side closure element. The sidewall free termini correspond to the patient side of the housing.

A first sensor system element $S_1$ resides in first cell 60. The first sensor system element is either an emitter 80 or a detector 82. Two or more second sensor system elements $S_2$ reside in one or more of the plurality of second cells 62. Each second sensor system element is the other of an emitter and a detector. In other words if the first sensor system element $S_1$ is an emitter 80, then the second sensor system elements $S_2$ are detectors 82, and vice versa. The physical system described in this specification and illustrated in the drawings is one in which the first sensor system element is an emitter 80, and the second sensor system elements are detectors 82.

Figure 5:
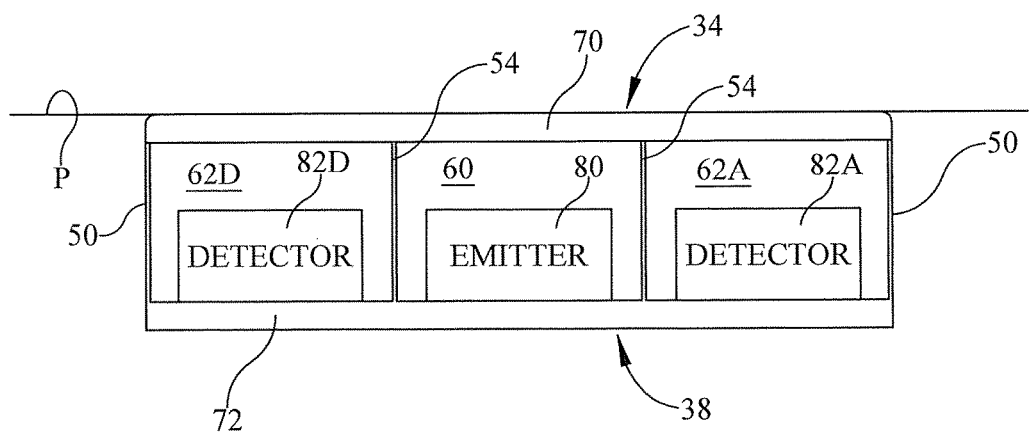
FIG. 5 is a sectional view along 5-5 of FIG. 3 showing an embodiment in which internal walls are common to neighboring cells, and showing the housing in a baseline state or configuration.

In one example the emitter and detectors are optical devices that emit and detect electromagnetic energy, not necessarily in the visible part of the electromagnetic spectrum. In another example the emitter and detector are acoustic devices that emit and detect acoustic energy. FIGS. 4-5 and 7 show the emitter and detectors secured to the inner surface of cover 72, however the emitters and detectors may instead be attached at other locations. Membrane 70, if present, is selected to offer as little interference as possible to signals emitted by the emitter and signals returning to the detector.

Figure 6:
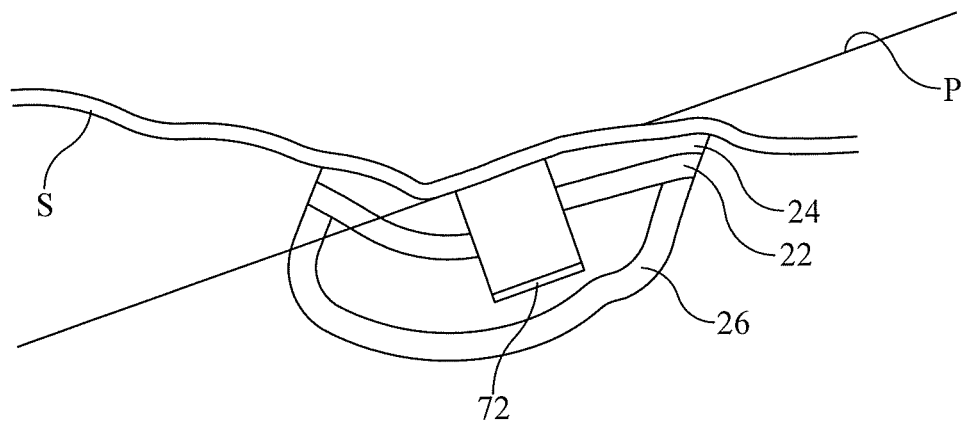
FIG. 6 is a view of the device of FIG. 1 attached to a patient's skin.

The patient side 34 of the housing has a baseline configuration. One possible baseline configuration is a planar geometry as suggested by plane P of FIGS. 1, 4, 5 and 7. However as seen in FIGS. 2 and 6, the patient side 34 of the housing is conformable to a non-baseline configuration. The non-baseline configuration results from the device 20 having been applied to a patient, e.g. attached to a patient by way of adhesive 24. As can be appreciated best from FIG. 6, contours of the patient's body contact the projecting portion of the housing and cause the patient side of the housing to deform in such a way as to deviate from the planar baseline configuration. Such deviation causes the patient side of the housing to form a seal with the patient's body. The seal serves the goal of ensuring that the emitter and detector are closely coupled to the patient's skin. In this context "closely coupled" does not require that the emitter and detector are in actual contact with the patient's skin. Instead, "closely coupled" means that a seal is formed so that the signal emitted from emitter 80 is constrained to first encounter the patient only within the area defined by the seal, and so that detectors 82 receive only those return signals that traverse through the sealed area.

In the example of FIGS. 2 and 6 the non-baseline, nonplanar geometry is an undulating shape. At other parts of the patient's body the non-baseline configuration may be a planar geometry which is nonparallel to the baseline plane.

Figure 8:
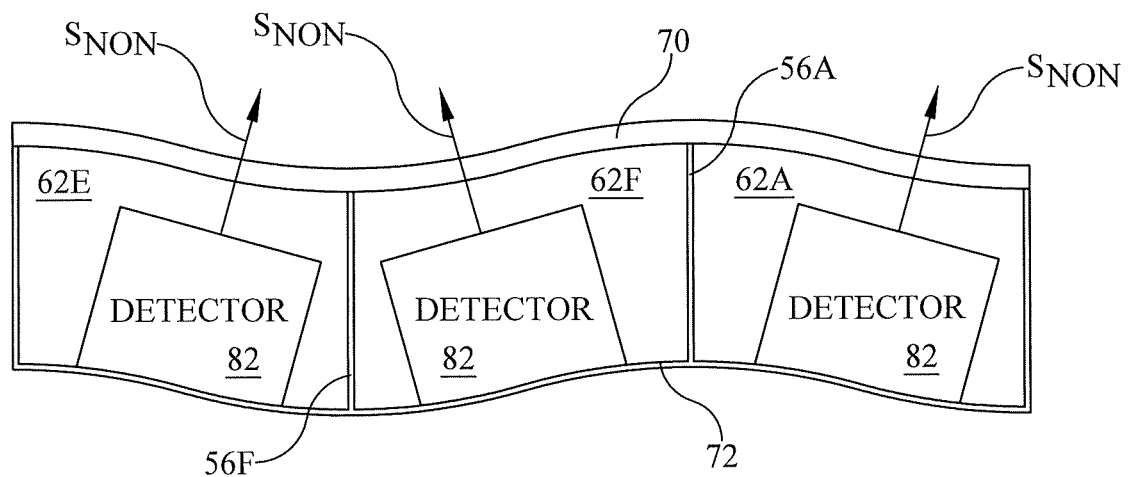
FIG. 8 is a view showing a non-baseline state of an embodiment of FIG. 4 in which the housing sidewalls are relatively rigid and the opposite side closure element is relatively flexible.

Referring now to FIGS. 4 and 8, in one embodiment the sidewalls are relatively rigid, and cover 72 is relatively flexible. As a result when the housing is deformed from the baseline configuration (FIG. 4) to the non-baseline configuration (FIG. 8), the walls exhibit relatively little flexure, and the cover at the opposite side of the housing takes on a deformed shape similar to that of patient side 34. A cross section taken along 5-5 of FIG. 3 would have an appearance similar to FIG. 8.

Cells 60, 62 have a baseline relationship with respect to each other, and a nonbaseline relationship with respect to each other. The nonbaseline relationship differs from the baseline relationship. The baseline relationship of FIG. 4 is one in which the lines of sight $S_{BASE}$ of the first and second sensor system elements $S_1$, $S_2$ are substantially parallel to each other. The nonbaseline relationship of FIG. 8 is one in which the lines of sight $S_{NON}$ of the first and second sensor system elements are not all substantially parallel to each other. The non-baseline line of sight of at least some of the sensor system elements differs from that same element's baseline line of sight.

Figure 9:
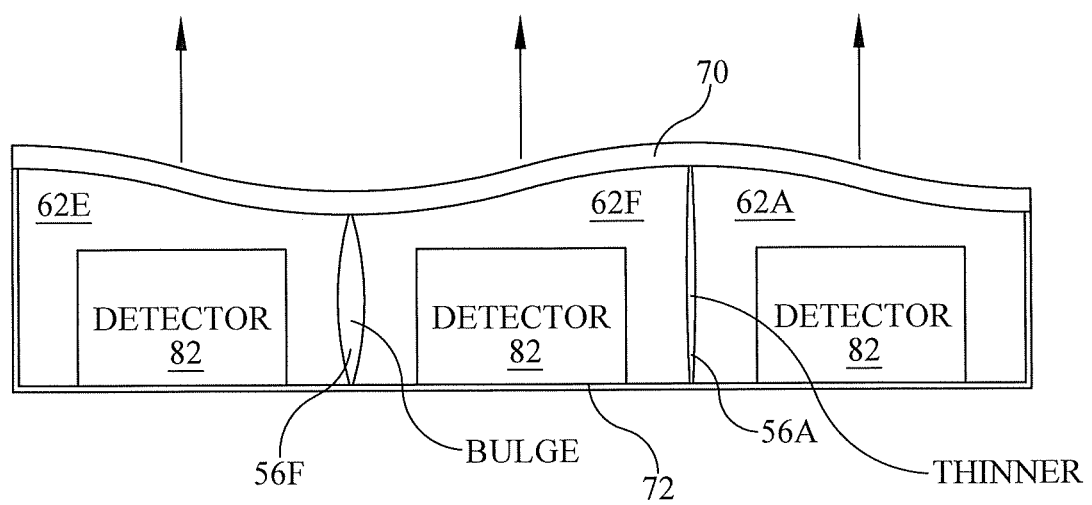
FIG. 9 is a view showing a non-baseline state of an embodiment of FIG. 4 in which the housing sidewalls are relatively elastic in the longitudinal direction and the opposite side closure element is relatively rigid.

Referring to FIGS. 4 and 9, in another embodiment the sidewalls are relatively elastic in the longitudinal direction, and cover 72 is relatively rigid. As a result when the housing is deformed from the baseline configuration (FIG. 4) to the nonbaseline configuration (FIG. 9) the sidewalls stretch (e.g sidewall 56A) or compress (e.g. sidewall 56F) in the longitudinal direction, and cover 72 exhibits relatively little shape change relative to the baseline of FIG. 4. A cross section taken along 5-5 of FIG. 3 would have an appearance similar to FIG. 9.

In the embodiment of FIGS. 4 and 9 cells 60, 62 have a baseline relationship with respect to each other, and a nonbaseline relationship with respect to each other. The nonbaseline relationship differs from the baseline relationship. The baseline relationship of FIG. 4 is one in which the intercell sidewalls each have a first length (although not necessarily the same first lengths). The nonbaseline relationship of FIG. 9 is one in which the deformation at patient side 34 of the housing causes one or more sidewalls to lengthen or shorten relative to the baseline length.

Figure 10:
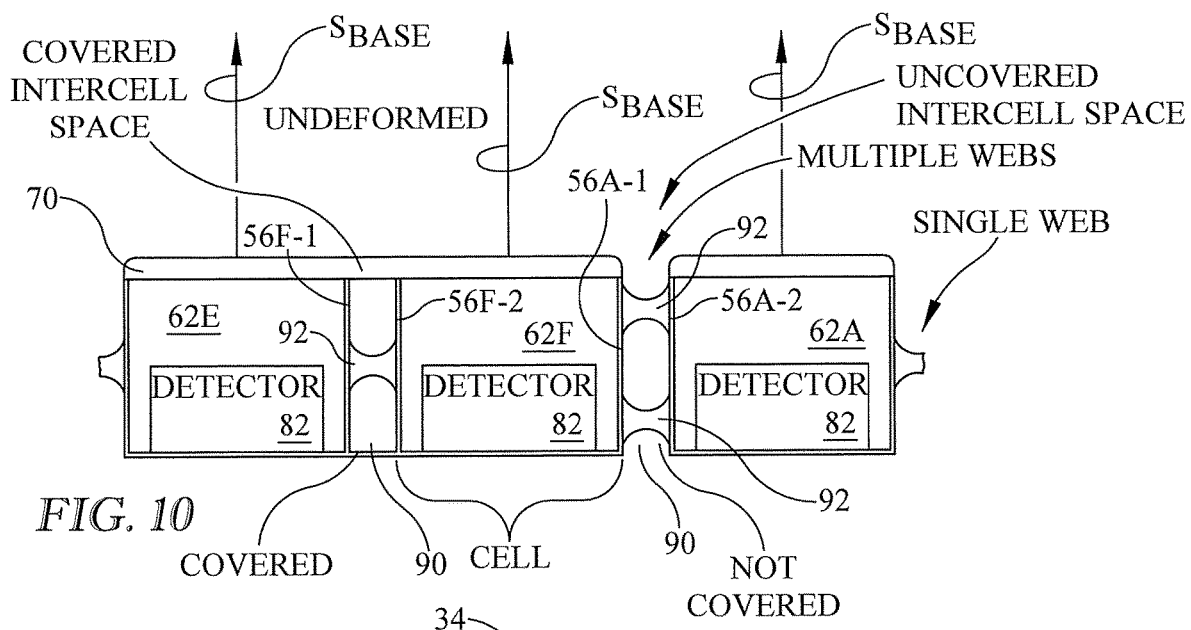
FIG. 10 is a view similar to FIG. 4 showing the baseline configuration of an embodiment of the housing in which at least some of the internal sidewalls are noncommon to adjacent cells.
Figure 11:
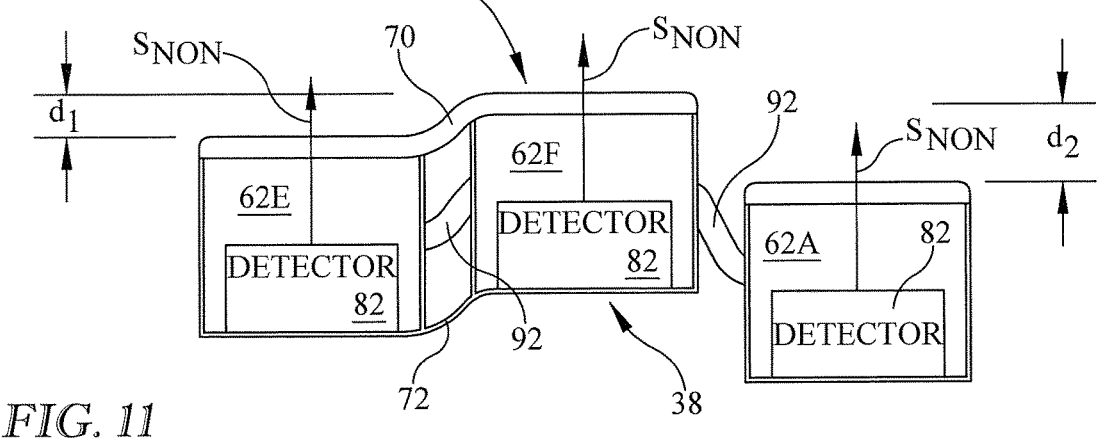
FIG. 11 is a view similar to FIG. 8 showing the non-baseline configuration of the embodiment of FIG. 10.
Figure 12:
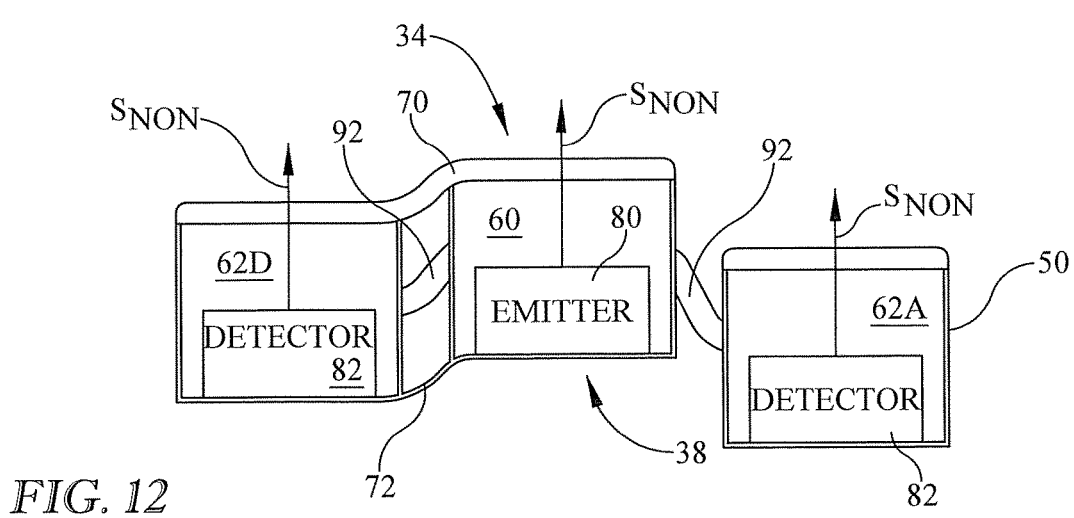
FIG. 12 is a view similar to FIG. 5 showing the non-baseline configuration of the embodiment of FIG. 10.

FIGS. 10-12 show the baseline configuration (FIG. 10) and non-baseline configuration (FIGS. 11, 12) of an embodiment of the housing in which at least some of the intercell sidewalls 54, 56 (e.g. 56F-1, 56F-2, 56A-1, 56A-2) are noncommon to adjacent cells. The noncommon intercell sidewalls are separated from each other by a space 90. One or more webs 92 extends across the space to connect neighboring intercell walls to each other. The illustrated embodiment includes both an opposite side cover 72 and a patient side membrane 70. The illustration depicts a number of variants, namely a single web variant (between sidewalls 56F-1 and 56F-2), a multiple web variant (between sidewalls 56A-1 and 56A-2), a variant in which the cover 72 and membrane 70 span across intercell space 90 (e.g. the space between sidewalls 56F-1 and 56F-2), and a variant in which the cover and membrane do not span across the intercell space (e.g. the space between sidewalls 56A-1 and 56A-2). The above described variants may be intermixed if desired however it is expected that a single variant of the webs (single web or multiple webs) and a single variant of the cover and membrane (spanning or nonspanning) would be selected for a commercial embodiment of the system.

In the embodiment of FIGS. 10-12 the cells have a baseline relationship with respect to each other, and a nonbaseline relationship with respect to each other. The nonbaseline relationship differs from the baseline relationship. The baseline relationship of FIG. 10 is one in which the cells are longitudinally aligned with each other. The nonbaseline relationship of FIGS. 11-12 is one in which the deformation at patient side 34 of the housing causes at least one cell to be displaced relative to the baseline so that it is nonaligned with the other cells. For example in FIG. 11 cells 62E and 62F are nonaligned by distance $d_1$; cells 62F and 62A are nonaligned by distance $d_2$. The non-baseline lines of sight are parallel or nearly parallel to the baseline lines of sight.

Figure 13:
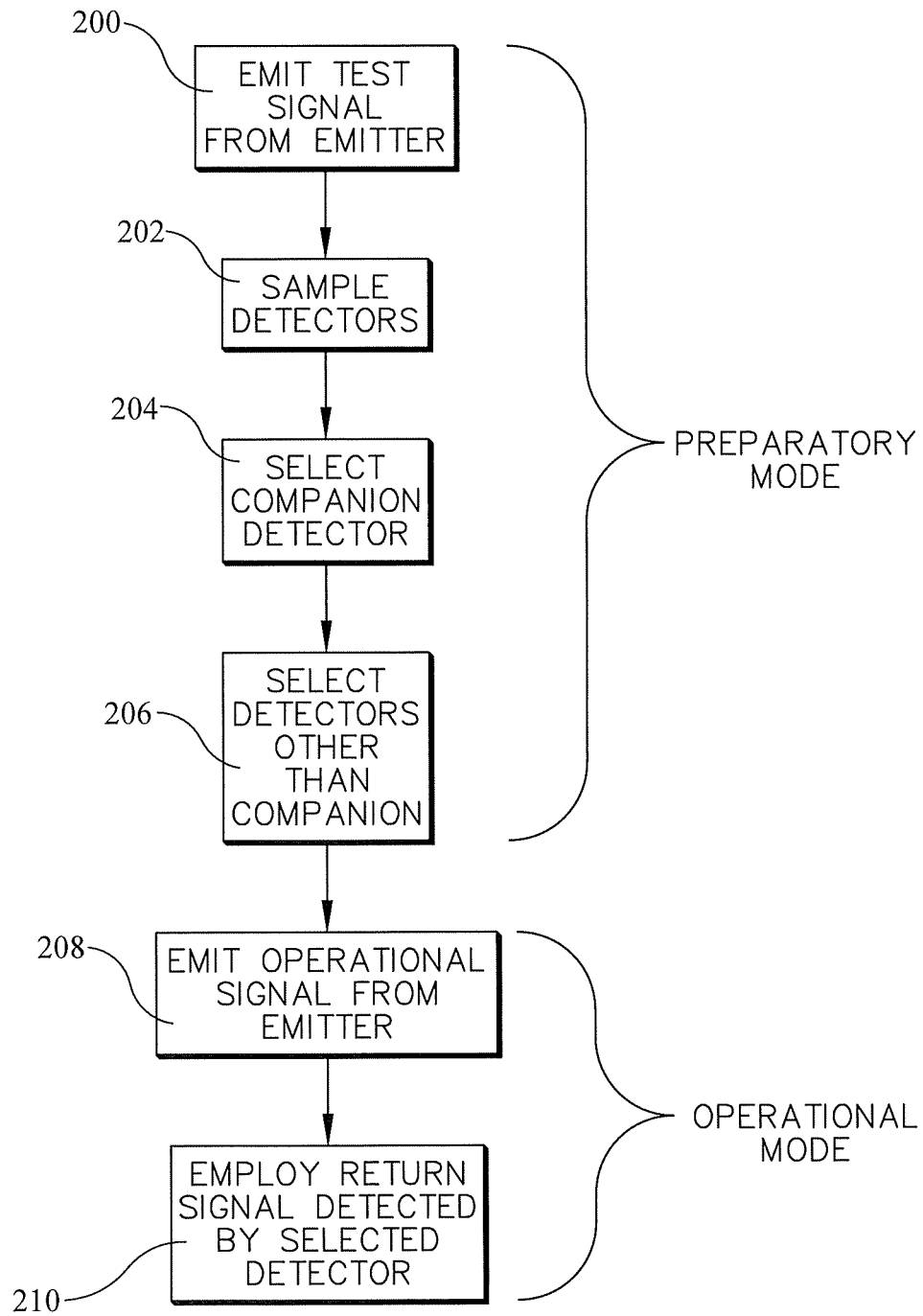
FIG. 13 is a block diagram showing a sequence of actions in which a single detector is selected from two or more detectors, and in which the selected detector is the only detector used to detect a return signal arising from emission of an operational signal from an emitter.

The sensor system also includes a processor 100 which executes machine readable instructions 102 (FIG. 1). The processor, operating according to the instructions, carries out a preparatory sequence of actions. Referring additionally to FIG. 13, in the preparatory mode of operation the processor causes the emitter to emit a test signal (or signals), for example emission of red and infrared light as is typically used for determining the oxygen saturation (SpO2) of a patient's hemoglobin (block 200). At block 202 the processor samples each detector for a return signal associated with the emitted signal. At block 204 the processor selects one of the detectors to be a companion to the emitter based on the quality of the return signal. Signal quality may be assessed on the basis of signal strength, signal to noise ratio or other relevant parameter(s). After identifying the detector which receives the best quality return signal the processor deselects, at least temporarily, all detectors other than the companion detector (block 206). Deselection involves reducing electrical power to the detectors other than the detector selected as the companion detector. In the limit deselection involves completely de-powering the detectors other than the detector selected as the companion detector.

The processor then transitions to and operates in an operational mode in which the first sensor system element (emitter 80) and the selected second sensor system element e.g. detector 82) are used to the exclusion of all other second sensor system elements. In the operational mode the system emits an operational signal from the emitter (block 208) and employs the return signal detected by the selected detector as a result of the emission from the emitter (block 210). Continuing with the example of determining a patient's SpO2, the system emits bursts of red and infrared light at block 208. The return signal resulting from the emission is sensed by the companion detector, the only detector receiving sufficient electrical power to operate satisfactorily. The system employs the return signal sensed by the companion detector in its determination of the patient's SpO2 (block 210).

Figure 14:
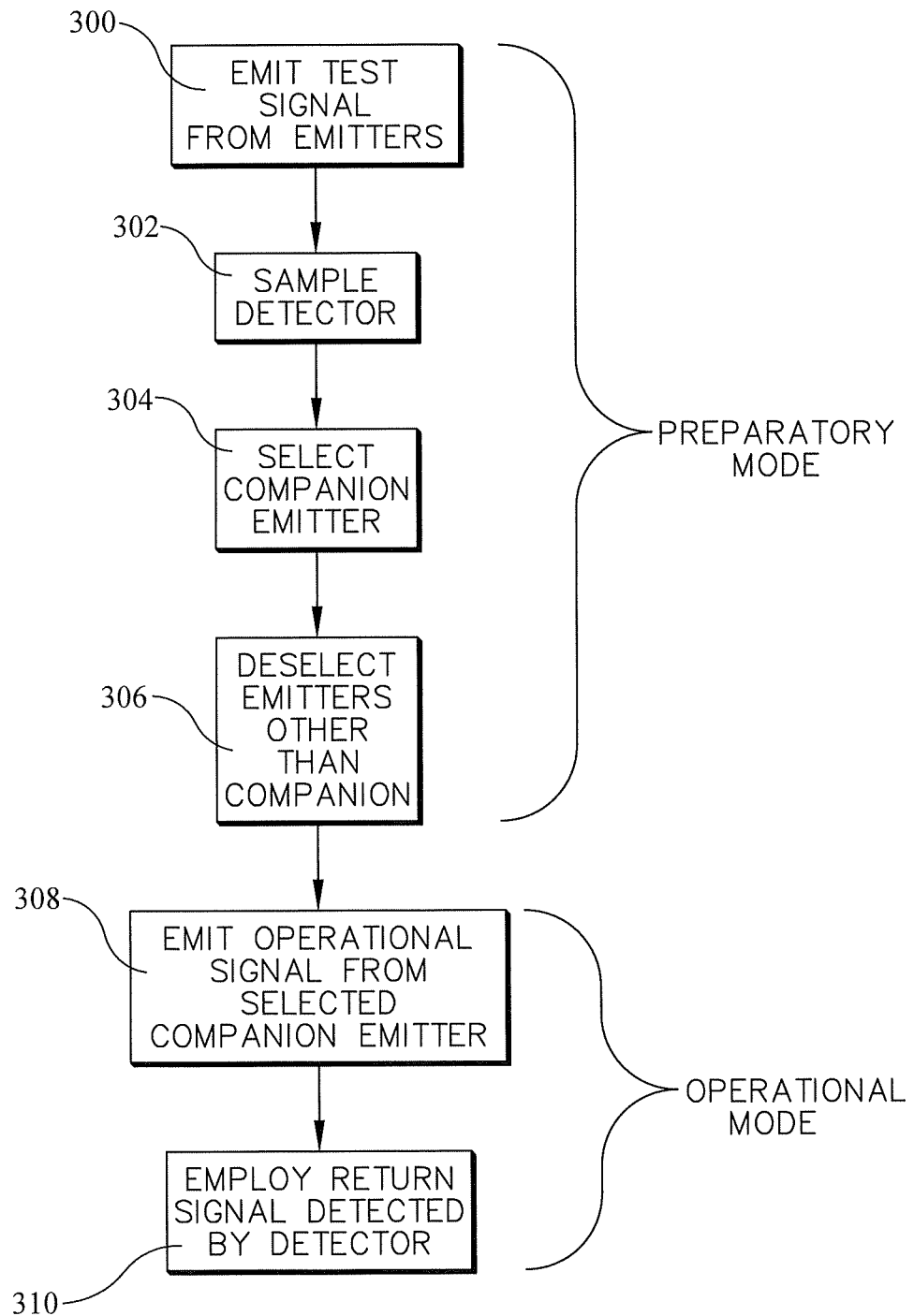
FIG. 14 is a block diagram showing a sequence of actions in which a single emitter is selected from two or more emitters, and in which the selected emitter is the only emitter used to emit an operational signal.

As previously noted, the sensor system can be arranged so that the first sensor system element is a detector and the second sensor system elements are emitters. Referring to FIG. 14, the processor causes each emitter to emit a test signal (block 300). At block 302 the system samples the single detector for a return signal associated with each emitted signal. At block 304 the system selects one of the emitters to be a companion to the detector based on quality of the return signal. After identifying the emitter which results in the best quality return signal at the detector the system deselects, at least temporarily, all emitters other than the companion emitter (block 306). In one embodiment deselection involves de-powering all emitters other than the emitter selected as the companion emitter.

The processor then operates in an operational mode. In the operational mode the system emits an operational signal from only the companion emitter (block 308) and employs the return signal detected by the single detector as a result of the emission from the emitter (block 310).

Whether the physical components of the system are a single emitter and multiple detectors or a single detector and multiple emitters, the instructions 102 may be written so that the processor periodically repeats the preparatory sequence. Doing so allows the system to adapt to changes that might have caused the previously selected companion emitter and detector to be less effective than some other emitter/detector pairing.

By operating in the manner described above the system conserves electrical power while also taking advantage of the emitter/detector pairing that yields the best quality signal at the detector. The spatial distribution of the second sensor system elements (emitters or detectors) cause the physiological parameter sensing system to be tolerant to suboptimal positioning on the patient's body.

The system described above includes either a single emitter and multiple detectors or a single detector and multiple emitters. Alternatively, the system may be configured to include multiple emitters and detectors. In that case instructions 102 will cause processor 100 to test the quality of the return signal arising from all possible emitter/detector pairings and will select the pairing that gives the best quality return signal as the companion emitter/detector pair to be used during the operational mode. As already described the system may periodically return to the preparatory mode.

Figure 15:
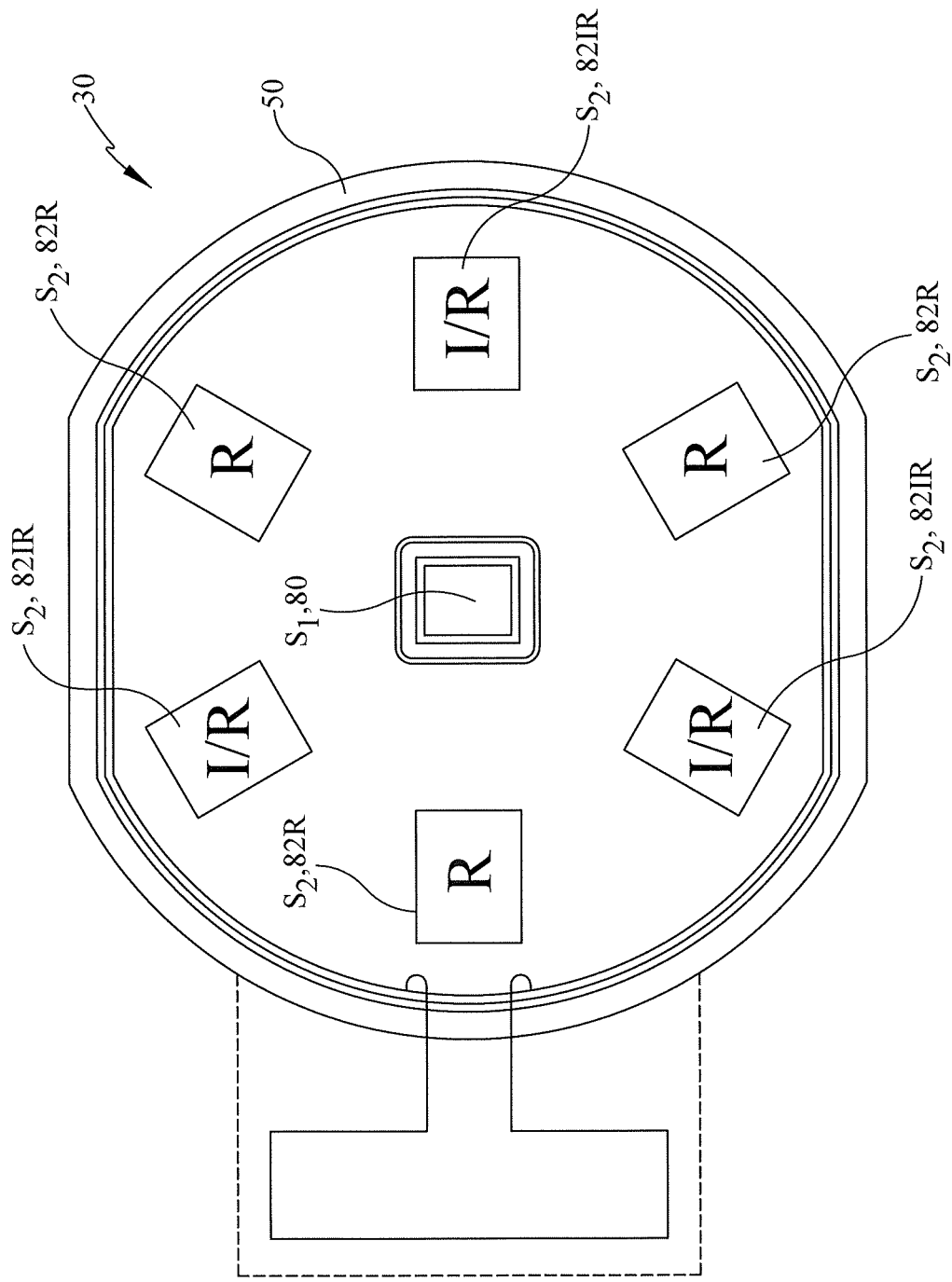
FIG. 15 is a view similar to that of FIG. 3 showing an embodiment of a physiological parameter sensing system specifically adapted for determining oxygen saturation ($SpO_2$) and having detectors optimized for detecting specified electromagnetic wavelengths.

FIG. 15 shows a specific embodiment for determining a patient's SpO2. In this embodiment the first sensor system element $S_1$ is an emitter, such as a photodiode 80, which emits alternate bursts of red and infrared light. The second sensor system elements $S_2$ are photodetectors 82. Photodetectors 82R are sensitive to red light. Photodetectors 82IR are sensitive to infrared light. Housing 30 of the embodiment of FIG. 15 includes perimeter sidewall 50 but not the hub sidewall 54 or radial sidewalls 56 depicted in other drawings. Nevertheless, hub and radial sidewalls could be included if desired.

Figure 16:
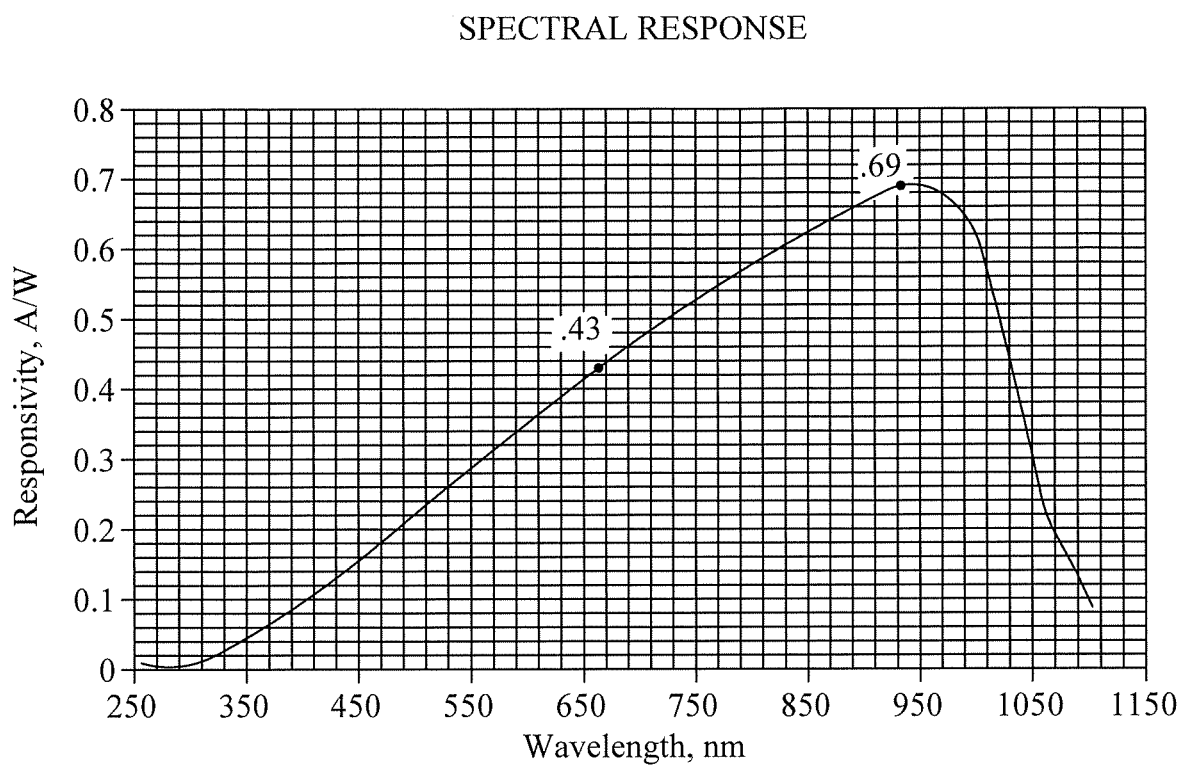
FIG. 16 is a graph showing performance of a sensor system element usable in the of FIG. 15 and which is optimized for infrared wavelengths.
Figure 17:
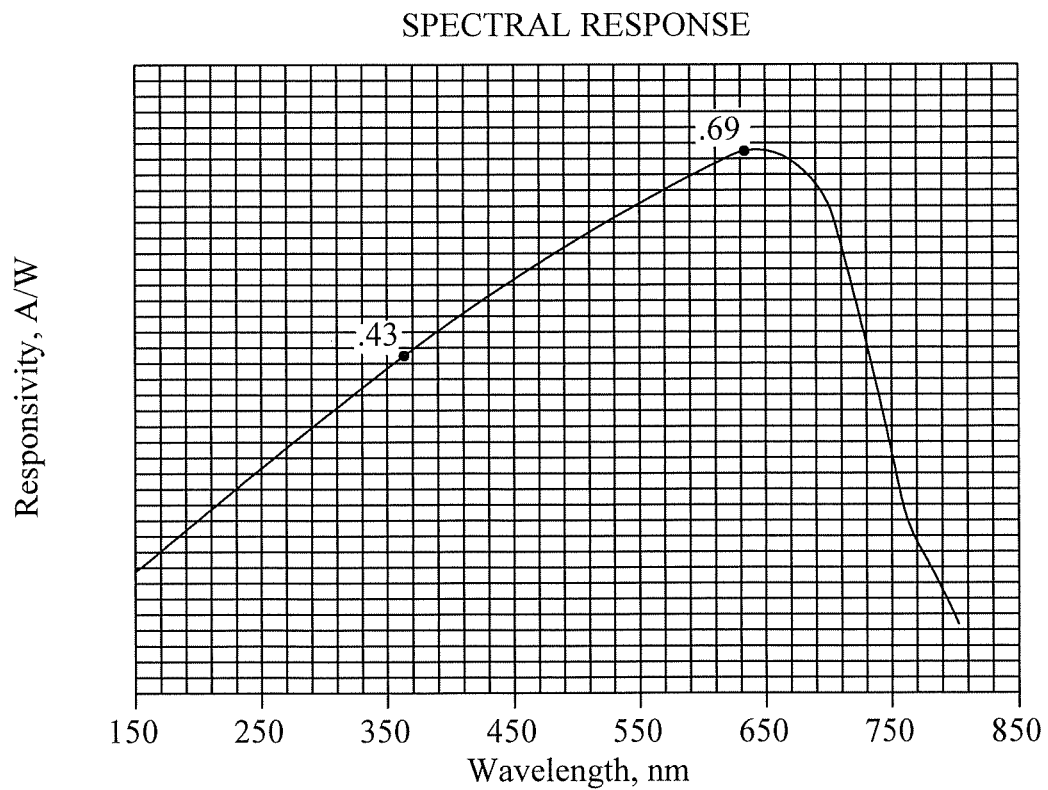
FIG. 17 is a graph showing performance of a sensor system element usable in the of FIG. 15 and which is optimized for red wavelengths.

Photodetectors 82 are adapted to exhibit a robust response to a specified wavelength of light. For example FIG. 16 shows the spectral response in amps per watt (A/W) of a photodetector whose peak response occurs at about 950 nm, which is in the infrared portion of the electromagnetic spectrum. FIG. 17 shows the spectral response of a photodetector whose peak response is at about 650 nm, which is in the red portion of the electromagnetic spectrum. Accordingly, the physiological parameter sensing system uses a detector whose performance is as shown in FIG. 16 as an infrared detector 82IR and uses a detector whose performance is as shown in FIG. 17 as a red detector 82R. The use of detectors optimized to respond best at specified wavelengths conserves electrical power. For example if the photodetector of FIG. 16 were used to detect both red and infrared wavelengths its peak response to red wavelengths would be only about 62% of its peak response to infrared (0.43/0.69=0.62) and would therefore be less useful than if detectors having the performance of FIG. 17 were used instead of those of FIG. 16 to detect red wavelengths. Alternatively, the emitting LED could be driven to a brighter level in order to get comparable responses to red and infrared from the detector of FIG. 16. However doing so increases the power demands of the system, which is contrary to what is desired.

Although this disclosure refers to specific embodiments, it will be understood by those skilled in the art that various changes in form and detail may be made without departing from the subject matter set forth in the accompanying claims.

What is claimed is:

1. A physiological parameter sensor system comprising:
   a housing having a patient facing side having a baseline configuration, an opposite side longitudinally spaced from the patient facing side, and a set of longitudinally extending sidewalls which cooperate with the patient facing side and the opposite side to define a first cell and a plurality of second cells which circumscribe the first cell;
   a first sensor system element residing in the first cell, the first sensor system element being an emitter;
   two or more second sensor system elements residing in the plurality of second cells, each second sensor system element being a detector;
   the patient facing side of the housing being conformable to a non-baseline configuration; and
   a processor adapted to:
      A) cause the emitter to emit a test signal,
      B) sample each detector for a return signal associated with the test signal,
      C) select one detector to be a companion detector to the emitter based on quality of the return signal, and
      D) deselect, at least temporarily, all detectors other than the companion detector;
   wherein some of the set of longitudinally extending sidewalls are intercell sidewalls common to adjacent cells; and
   wherein the intercell sidewalls are configured to stretch and compress in a longitudinal direction.

2. The sensor system of claim 1 wherein the baseline configuration is a plane, and the non-baseline configuration is a plane which is nonparallel to the baseline plane.

3. The sensor system of claim 1 wherein the baseline configuration is a plane and the non-baseline configuration is nonplanar.

4. The sensor system of claim 1 wherein the opposite side of the housing is a cover, and each sidewall extends longitudinally from the cover to a sidewall terminus which is joined to a closure element which defines the patient side of the housing.

5. The sensor system of claim 1 wherein the opposite side of the housing is a cover, and each sidewall extends longitudinally from the cover to a sidewall free terminus which defines the patient side of the housing.

6. The sensor system of claim 1 wherein steps A, B, C and D are a preparatory sequence and the processor is adapted to, subsequent to the preparatory sequence:
 E) cause the emitter to emit an operational signal, and
 F) employ the return signal detected by the selected detector as a result of the operational signal from the emitter.

7. The sensor system of claim 6 wherein the processor is adapted to periodically repeat the preparatory sequence.

8. The sensor system of claim 1 wherein the step of deselecting all detectors other than the companion detector is a step of de-powering all detectors other than the companion detector.

9. The sensor system of claim 1 wherein when the housing is applied to a patient the non-baseline configuration follows a contour of the patient.

10. The sensor system of claim 1 wherein the first sensor system element has a baseline line of sight and a non-baseline line of sight, and the nonbaseline line of sight differs from the baseline line of sight.

11. The sensor system of claim 1 wherein some of the sidewalls are noncommon intercell sidewalls connected to an adjacent intercell sidewall by a web.

12. The sensor system of claim 1 wherein:
 two or more of the plurality of second cells are longitudinal aligned in the baseline configuration; and
 at least one cell of the plurality of second cells is longitudinally nonaligned with other cells of the plurality of second cells in the non-baseline configuration.

13. The sensor system of claim 1 wherein:
 the first cell is a central cell;
 the plurality of second cells are radially adjacent to the first cell;
and
 the sensor system includes the processor adapted to select a detector/emitter pair and to control an operational mode in which the emitter and detector of the selected pair are used, at least temporarily, to the exclusion of all other emitters and detectors.

* * * * *